US00PP07770P

United States Patent [19]

Saville

[11] Patent Number: Plant 7,770

[45] Date of Patent: Jan. 21, 1992

[54] MINIATURE ROSE PLANT NAMED SAVAHALO

[75] Inventor: F. Harmon Saville, Rowley, Mass.

[73] Assignee: Nor'East Miniature Roses, Inc., Rowley, Mass.

[21] Appl. No.: 591,556

[22] Filed: Oct. 1, 1990

[51] Int. Cl.[5] ..... A01H 5/00

[52] U.S. Cl. ..... Plt./8

[58] Field of Search ..... Plt./8

*Primary Examiner*—James R. Feyrer

*Attorney, Agent, or Firm*—Christie, Parker & Hale

[57] ABSTRACT

A new miniature rose plant producing yellow flowers.

1 Drawing Sheet

SUMMARY OF THE INVENTION

The present invention relates to a new and distinct variety of rose plant of the miniature rose class, which was originated by my crossing as seed parent the floribunda variety known as "Arthur Bell" and as pollen parent the variety known as "Rainbow's End" (U.S. Plant Pat. No. 5,482). The varietal denomination of this new rose is "Savahalo".

Among the novel characteristics possessed by this new variety which primarily distinguishes it from its parent and all other varieties of which I am aware are its unusual yellow flowers. Flowers open well and lighten upon aging.

Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF THE PREFERRED EMBODIMENT

The following is a detailed description of my new variety, with color terminology in accordance with The Royal Horticultural Society Color Chart (R.H.S.C.C.). The terminology used in color description herein refers to plate numbers in the aforementioned color chart, e.g., "4A" is plate "4A" of The Royal Horticultural Society Color Chart.

Parentage: Seedling.

*Seed parent.*—"Arthur Bell".

*Pollen parent.*—"Rainbow's End".

Class Miniature.

The following observations are made of specimens grown under glass in Essex County, Mass., during the month of July.

FLOWER

Blooming habit: Continuous.

A. Bud:

(1) *Size.*—Medium.

(2) *Form.*—Ovate.

(3) *Color.*—As sepals divide, bud color is near 4A.

(4) *Sepals.*—Medium length, smooth, lightly foliated.

(5) *Peduncle.*—Length — about ¾ inch. Aspect — straight. Strength — erect. Color — near 145A to 144B.

B. Bloom:

(1) *Size.*—Average size when fully expanded — about 1¾ inches.

(2) *Borne.*—Usually singly.

(3) *Form.*—Cupped at first, becoming flat; outer petals quill to points.

(4) *Petalage.*—Number of petals under normal conditions — about 24 to 26.

(5) *Color.*—After sepals fall and petals unfurl, predominant flower color is attractive yellow coloring which may include a subtle green cast. General tonality from a distance is attractive yellow coloring. Color at point of petal attachment is near 6A. As flowers age, yellow flower coloring lightens through the range of near 9D to 12C to 12D.

C. Petals:

(1) *Texture.*—Average.

(2) *Appearance.*—Inside velvety and outside satiny.

(3) *Form.*—Broad, fan shaped outer petals with pointed apices.

(4) *Arrangement.*—Regularly arranged, imbricated.

(5) *Petaloids in center.*—Medium.

(6) *Persistence.*—Drop off cleanly.

(7) *Fragrance.*—Slight.

(8) *Lasting quality.*—Average.

REPRODUCTIVE ORGANS

A. Stamens, filaments and anthers:

*Arrangement.*—Regularly arranged around styles.

*Color.*—Filaments near 17A.

B. Pollen:

*Color.*—Near 23B.

C. Styles: Medium length, even.

D. Stigmas:

*Color.*—Near 154D.

E. Hips: None observed.

PLANT

A. Form: Upright, compact.

B. Growth: Very vigorous.

*Height attained.*—About 14 to 18 inches.

C. Foliage: Compound 5 to 7 leaflets.

(1) *Size.*—Medium.
(2) *Quantity.*—Abundant.
(3) *Color.*—New foliage: Upper side — near 144A. Under side — near 139D. Old foliage: Upper side — near 137A. Under side — near 138B.
(4) *Shape.*—Oval, pointed.
(5) *Texture.*—Similar to "Arthur Bell", raised between veins; glossy; under side is matte.
(6) *Edge.*—Serrate.
(7) *Serration.*—Relatively fine.
(8) *Leaf stem.*—Color — near 199B. Under side — 145C.
(9) *Stipules.*—Medium length.
(10) *Resistance to disease.*—Blackspot — Average. Mildew — Average. Rust — Average.

D. Wood:
(1) *New wood.*—Color — near 144C. Bark — smooth.

(2) *Old wood.*—Color — near 146C. Bark — smooth.

E. Thorns:
*Quantity (main stalk).*—Ordinary.
*On laterals from stalk.*—None.
*Form.*—Pointed, curved and angled downward.
*Length.*—Medium.
*Color.*—Near 194D.
*Position.*—Irregular.
*Prickles.*—Few.

F. Winter hardiness: Needs protection in severe climates.

I claim:

1. A new and distinct variety of rose plant of the miniature rose class, substantially as shown and described, characterized particularly by attractive yellow flowers.

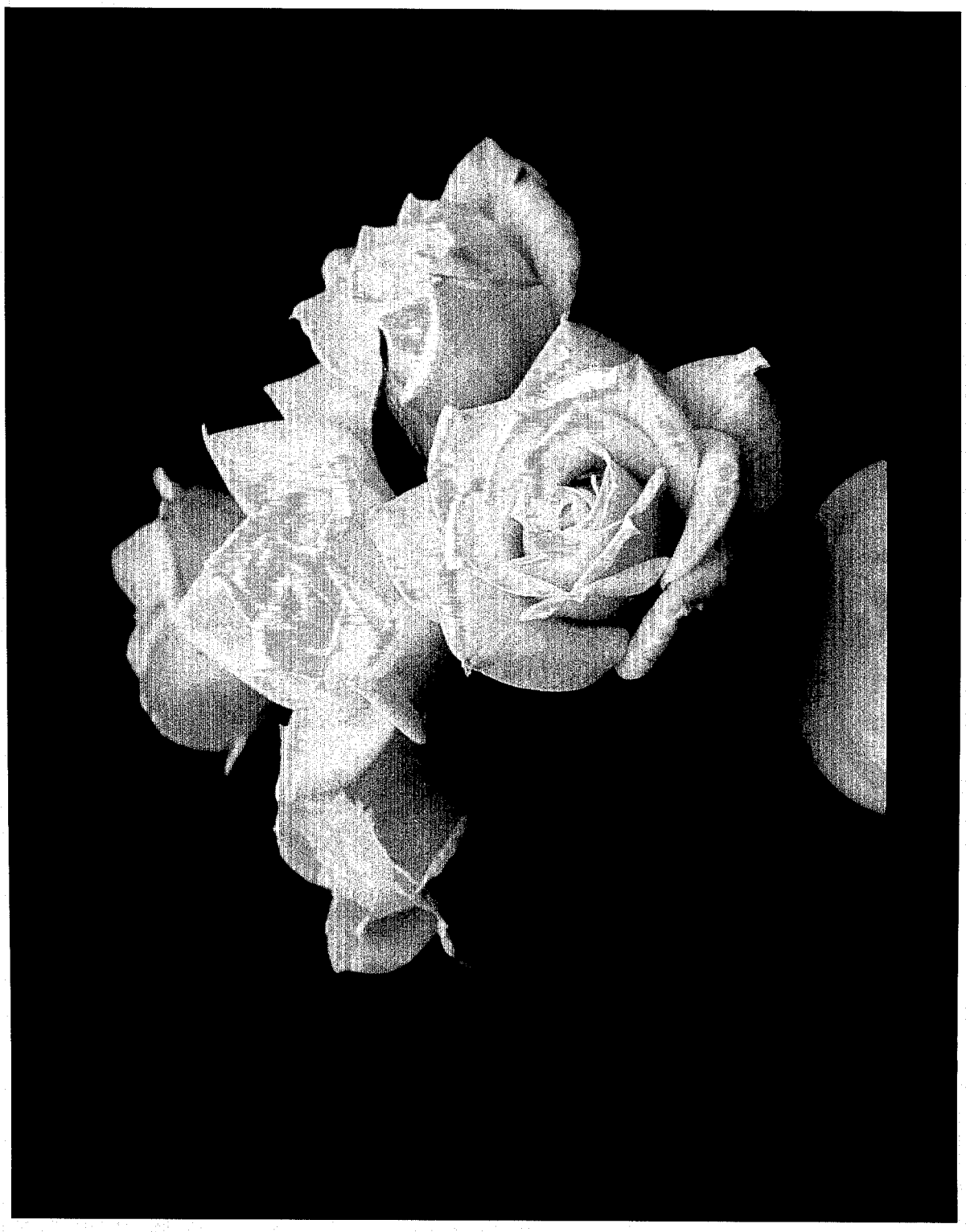

* * * * *